(12) United States Patent
Buschke et al.

(10) Patent No.: US 7,577,533 B2
(45) Date of Patent: Aug. 18, 2009

(54) ULTRASONIC INSPECTION APPARATUS FOR INSPECTING A WORKPIECE

(75) Inventors: Paul Buschke, Hürth (DE); Bernd Kirchner, Erftstadt (DE)

(73) Assignee: Agfa NDT GmbH, Hürth (DE)

( * ) Notice: Subject to any disclaimer, the term of this patent is extended or adjusted under 35 U.S.C. 154(b) by 106 days.

(21) Appl. No.: 10/530,797

(22) PCT Filed: Sep. 24, 2003

(86) PCT No.: PCT/DE03/03164

§ 371 (c)(1),
(2), (4) Date: Sep. 26, 2005

(87) PCT Pub. No.: WO2004/036144

PCT Pub. Date: Apr. 29, 2004

(65) Prior Publication Data

US 2006/0109002 A1    May 25, 2006

(30) Foreign Application Priority Data

Oct. 10, 2002   (DE) ............................... 102 47 257

(51) Int. Cl.
*G06F 19/00* (2006.01)
(52) U.S. Cl. .......................................... 702/39; 702/35
(58) Field of Classification Search ................. 73/1.82, 73/570, 584, 598, 600; 702/35, 39, 103, 702/159, 171
See application file for complete search history.

(56) References Cited

U.S. PATENT DOCUMENTS 3,115,770 A * 12/1963 Cram et al. .................... 73/600

(Continued)

FOREIGN PATENT DOCUMENTS

DE    102 47 257.2    4/2002

(Continued)

OTHER PUBLICATIONS

Ramuhalli, P; Kim, J; Udpa, S; "Multichannel Signal Processing Methods for Ultrasonic Nondestructive Evaluation"; Proceedings Sensor Array and Multichannel Signal Processing Workshop 2002; Aug. 4-6, 2002; pp. 229-233.*

(Continued)

*Primary Examiner*—Edward R Cosimano
*Assistant Examiner*—Douglas N Washburn
(74) *Attorney, Agent, or Firm*—McCarter & English, LLP

(57) ABSTRACT

The invention relates to an ultrasound control device for non-destructively inspecting a workpiece. The inventive ultrasound control device comprises a transmitting-receiving sensor provided with an element for connecting to the input surface of a controlled workpiece, a transmitter which is connected to the sensor and sends pulses produced thereby to said sensor, a receiver connected to the sensor and a screen which is connected to the receiver for displaying electric echo signals received by the receiver. The sensor transmits ultrasound pulses which, on one hand are reflected by the input surface and return to said sensor, and penetrate into the workpiece and are reflected at least once by the back wall thereof, on the other hand. Said ultrasound control device also comprises a bar display for visualising the received electric echo signals. At least one signal value displayed on said display in a real time results from one of electric echo signals reflected by the input surface: an input echo reflected by the input surface, at least one echo from the back wall and/or one signal calculated on the basis of several echoes reflected thereby.

13 Claims, 3 Drawing Sheets

U.S. PATENT DOCUMENTS

Figure 1:
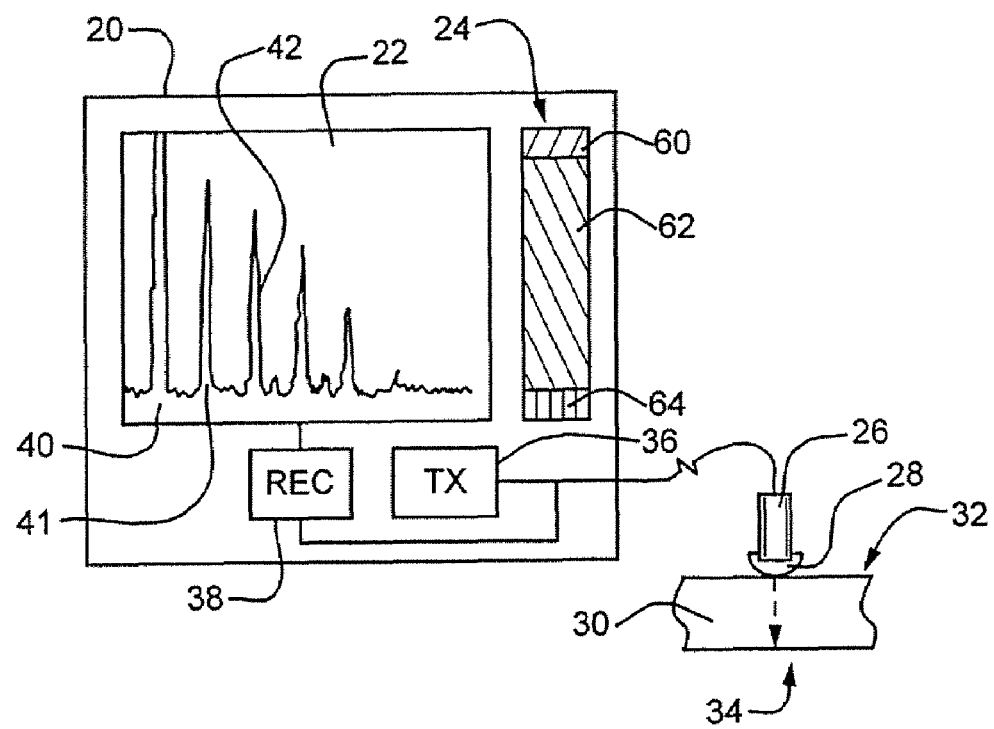

| | | | |
|---|---|---|---|
| 4,055,989 A | 11/1977 | Henry, Jr. et al. | |
| 4,275,596 A * | 6/1981 | Horn | 73/607 |
| 5,717,142 A | 2/1998 | Schafer | |
| 6,247,353 B1 * | 6/2001 | Battenberg et al. | 73/40.5 A |
| 6,938,488 B2 * | 9/2005 | Diaz et al. | 73/597 |

FOREIGN PATENT DOCUMENTS

| | | |
|---|---|---|
| GB | 2062383 | 5/1981 |
| JP | 03 125964 | 5/1991 |

OTHER PUBLICATIONS

International Search Report of PCT Application No. PCT/2004/036144, Apr. 5, 2004.

* cited by examiner

ULTRASONIC INSPECTION APPARATUS FOR INSPECTING A WORKPIECE

FIELD OF THE INVENTION

The invention relates to an ultrasonic inspection apparatus for non-destructive inspection of a workpiece, said ultrasonic inspection apparatus having a transmit/receive probe comprising a couplant for coupling to an entrance surface of the workpiece, a transmitter connected to said probe and generating transmit pulses which it then delivers to said probe, a receiver connected to said probe and a monitor that is connected to said receiver for displaying electric echo signals received by said receiver. The probe emits ultrasonic pulses that, on the one side, are reflected at the entrance surface back to the probe and on the other side penetrate the workpiece where they are reflected at least once at a backwall of the workpiece.

Description of the Related Art

For ultrasonic non-destructive inspection of a workpiece, suited inspection apparatus are known. General reference is made to the German book J. and H. Krautkrämer, Werkstoffprüfung mit Ultraschall ("Material Inspection with Ultrasounds"), fourth edition. The pulse-echo technique is used for this purpose. The probe emits ultrasonic pulses preferably periodically and receives next the echo signals of these emitted ultrasonic pulses. Generally, the echo signal of the entrance surface is particularly strong and exceeds the other echo signals. The other echo signals originate from the workpiece, more specifically from the backwall of the workpiece, where they are reflected at least once. Inasmuch, the inspection method is suited for workpieces the entrance surface of which is oriented to be substantially parallel to the backwall so that the ultrasonic pulse is reflected back and forth several times within the workpiece. This is the case with ultrasonic inspection of spot welded joints of sheet metal parts for example.

The echo signals received are displayed on the monitor. They are displayed as what is termed an A-scan in which the voltage values of the echo signals received are plotted down the side of the diagram whereas time is plotted on the horizontal axis. As the pulse is reflected back and forth several times between entrance surface and backwall, a sequence of evenly spaced echo signals is obtained the amplitude of which generally decreases with time.

The ultrasonic inspection of the type mentioned herein above may serve to merely determine the wall thickness between entrance surface and backwall. It may however also serve to determine the quality of a spot weld joint or to detect flaws. In all such cases it is necessary to be informed of the quality of the coupling to the probe at the entrance surface and also preferably of the quality of the echo sequence.

For inspecting spot weld joints on the bodywork of an automotive vehicle, it is desirable to achieve high inspection speed. To inspect all the spot welds of a bodywork, typically two to three thousand welds are to be inspected. For each point it has to be made certain that coupling is good and that the echo sequence is of sufficient quality.

Experience has shown that with the prior art ultrasonic inspection apparatus it is extremely difficult to care for both good coupling and good echo sequences. This places high demands on the operator of the ultrasonic inspection apparatus. Only experienced and well trained operators are capable of inferring from an A-scan both good coupling and good backwall echo sequence and possibly also a flaw echo sequence.

Moreover, the ultrasound parameters such as sound velocity, probe lead body, amplification, beginning of the image and image width have to be set with the greatest possible accuracy. Finally, the quality of the sheet joint, more specifically the thickness of each of the connected sheets, the number of the sheet joints, the sound attenuation in the material and in the weld point affect the inspection result, meaning the A-scan.

Using the prior art method, an operator couples an ultrasonic probe to a to-be-tested spot weld joint and moves the probe in at least two solid angles and in absolute terms with respect to the weld point until good backwall echo sequence with simultaneously good entrance signal is achieved. He moves the probe until a good enough quality of the A-scan is obtained, thus aiming at achieving a good quality A-scan.

SUMMARY OF THE INVENTION

This is where the invention comes in. It seeks to facilitate the work performed by the operator and to provide him with an ultrasonic inspection apparatus that clearly indicates the quality of a coupling and of an echo sequence without the operator having to mind details in the A-scan.

In view of the ultrasonic inspection apparatus of the type mentioned herein above, this object is accomplished by providing said ultrasonic inspection apparatus having, in addition to the display displaying the received electric echo signals, a bar display showing at least one signal value in real time with said signal being derived from one of the following echo signals: the entrance echo reflected at the entrance surface, at least one backwall echo and/or one signal calculated from a plurality of backwall echoes.

The bar display outputs at least one signal value, for example a signal value for the entrance echo or a signal value for the quality of the backwall echo sequence. In the last mentioned case, an evaluation of a plurality of backwall echo signals is carried out and a signal value, which is calculated by taking the mean of a plurality of backwall echoes, is delivered.

The respective at least one signal value shown on the bar display is directly indicative of the quality. In practice, when performing the inspection, the operator can substantially concentrate on the A-scan and keep an eye on the bar display besides; he needs not direct his full attention toward the bar display. The information the bar display shows is in principle contained in the A-scan as well. Thus shown on the bar display, the corresponding indications are allowed to be better registered by the operator and are displayed more prominently. Details of the A-scan are easy to distinguish in the bar display where they are displayed in a more dramatic way, more specifically in a particular colour so as to be readily noticeable. This facilitates the ultrasonic inspection and more specifically aids in keeping the attention of the operator for a long time.

When aiming at achieving a good quality A-scan, the bar display changes just like the A-scan changes in real time. This means that, after each reset of the probe, the operator immediately receives the ultrasound signal associated with the selected orientation of the probe. If the coupling conditions change during reorientation, this will immediately translate into another bar display.

It is preferred that the bar display not only displays one signal value but two or three signal values. The different signal values are shown in different colours, such as in the colours of a traffic light or in other clearly differing colours such as yellow, green, blue. The bar display is chosen to be sufficiently wide for good visibility. Typical widths are at least 10 mm, with widths of between 20 and 30 mm being preferred. The bar display may be a separate display, for example a narrow, elongate colour LCD, but it may also be a stripe that has been left unoccupied by a display unit used for displaying the A-scan so that A-scan and bar display appear side by side on the same monitor screen. Colour monitors other than LCD-displays have also proved efficient, such as plasma displays for example.

In principle, the bar display can be built from a series of light-emitting diodes. Light-emitting diodes of different colours are used so that a plurality of bar displays may be arranged side by side. It is preferred though that the different signal values be displayed in different colours one above the other.

Evaluation of the signal sequence of the A-scan does not pertain to the present invention. The present invention is rather directed at assisting the operator in achieving a good quality A-scan by providing a display in the form of a bar. Nowadays, such type displays are usual with Hi Fi apparatus, mobile phones and in the field of presentation graphics as it may for example be set up in a computer.

In the preferred implementation of the invention, a signal value of the bar display is associated with the quality of the entrance echo. Good coupling is the primary prerequisite for good ultrasonic measurement. Good coupling is achieved when the entire bar display is visibly illuminated, meaning when the signal applied is 100%. The other signal values are chosen to be less than 100% so that a coupling of good enough quality may always be recognized and that the other signal values can still be shown on the same display screen.

A superimposed bar of a different colour is used as the second signal value indicative of the quality of the backwall echo sequence. The height of the bar is indicative of the quality of the backwall echo sequence. If the bar reaches or exceeds a rating threshold to be determined by the adjuster, e.g., 60% or 80%, the quality of the backwall echo sequence is sufficient. In this case, the associated A-scan can be used for rating the spot weld joint. In addition thereto, a third colour bar may be shown, said third bar being smaller than the colour bar of the signal value indicative of the quality of the backwall echo sequence. Said third colour bar may for example be indicative of the quality of the flaw echo sequence. As it always remains beneath the bar of the backwall echo sequence, it may be easily recognized as such. Practical tests have shown that it is readily possible for an operator to distinguish three superimposed bars on one unique bar display.

In a preferred developed implementation, the bar display is disposed in the nearest possible proximity to the monitor or is part thereof. The operator may thus easily associate it with the A-scan without having to direct its full attention toward the bar display.

It is preferred that the bar display extends across the time axis of the A-scan on the monitor. Preferably, the bar display is of the same height as the monitor and is oriented to be parallel to the monitor so that the signal values on the bar display increase in the same direction as the electric voltages of the signals of the A-scan.

BRIEF SUMMARY OF THE INVENTION

Figure 2:
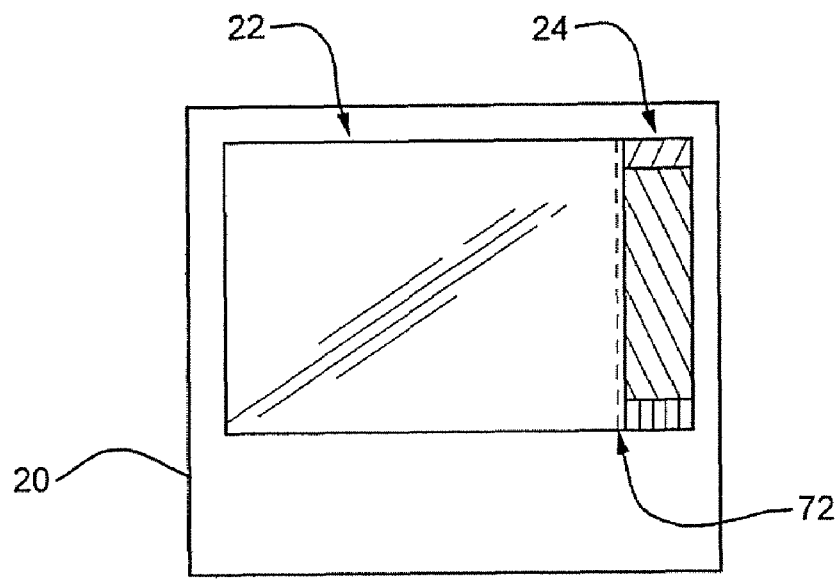
Figure 3:
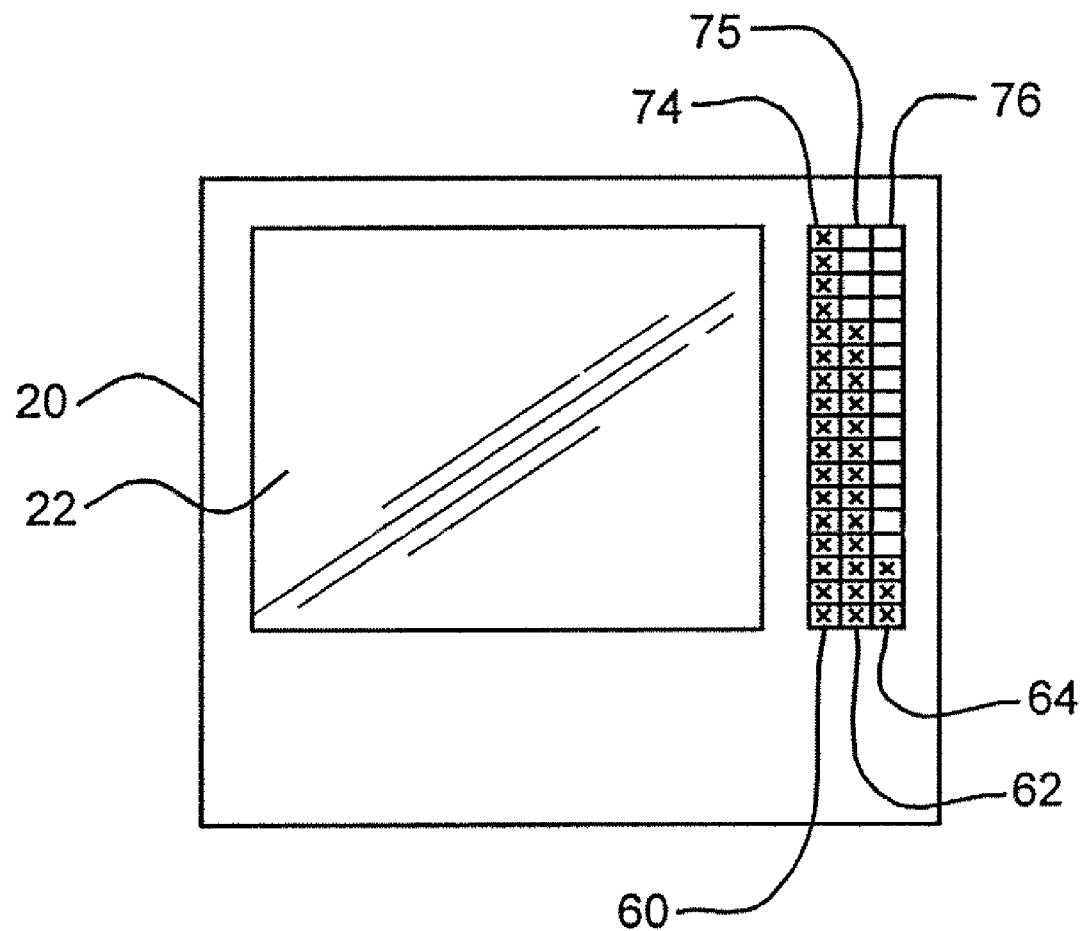
Figure 4:
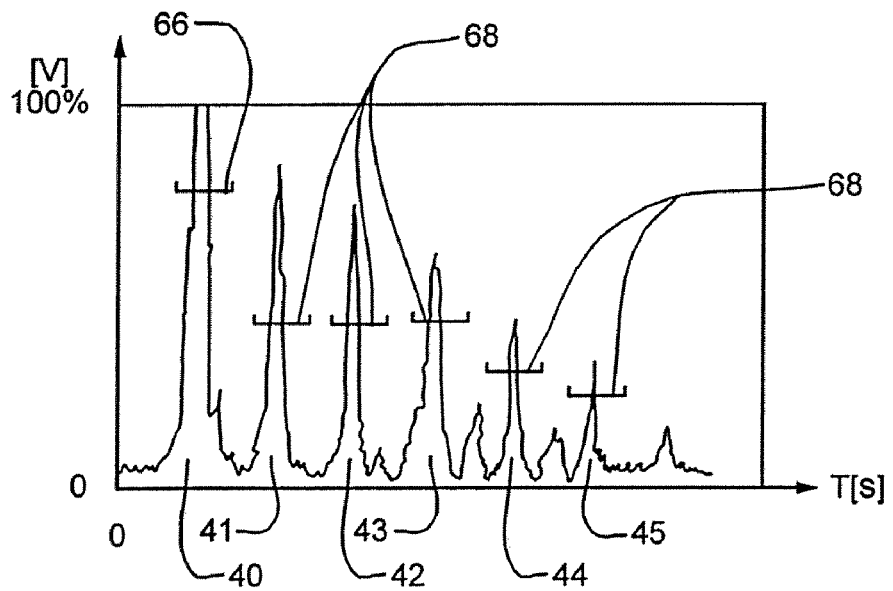
Figure 5:
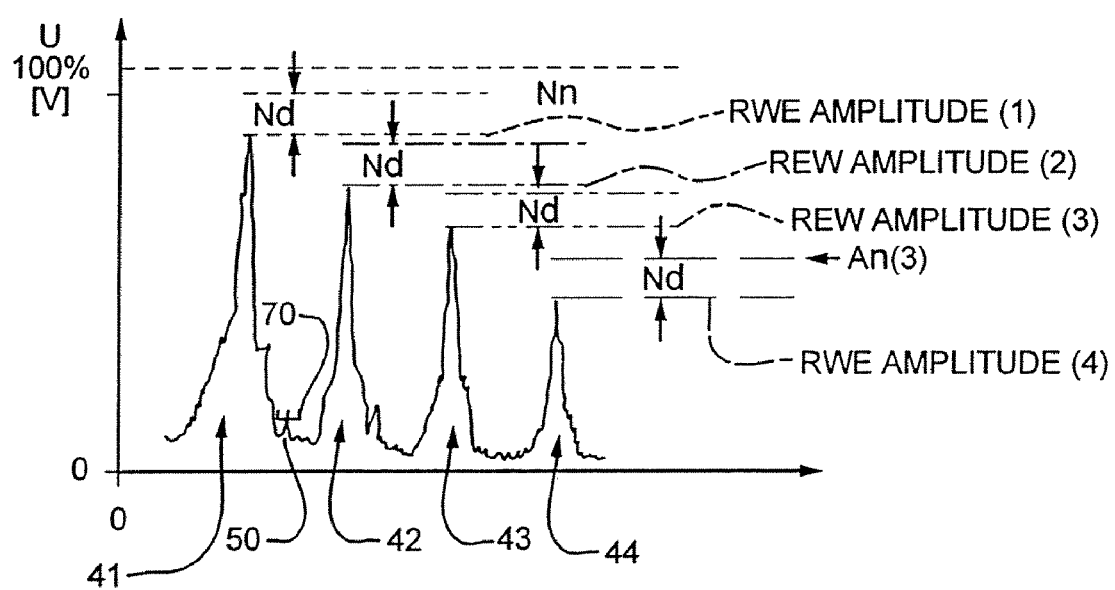

Other features and advantages will become more apparent upon reviewing the appended claims and the following non restrictive description of embodiments of the invention, given by way of example only with reference to the drawing. In said drawing:

FIG. 1 is a schematic illustration of an ultrasonic inspection apparatus of the invention, FIG. 2 is a schematic illustration like FIG. 1, but in another implementation and without probe and workpiece, FIG. 3 is an illustration like FIG. 2 of a third implementation of the inspection apparatus, FIG. 4 is a schematic illustration of an echo sequence similar to the image shown in FIG. 1, as it typically appears on a monitor and FIG. 5 is a schematic illustration of an echo sequence without entrance echo and for backwall echoes as it typically appears on a monitor for a better understanding of the method of normalizing an echo sequence.

DETAILED DESCRIPTION

In a housing 20 of an ultrasonic inspection apparatus there is disposed a monitor 22, which may for example be an LCD-display. A bar display 24 is disposed immediately beside it and parallel thereto. Said bar display also is an LCD-display. The bar display 24 has the same height dimension as the monitor 22. The bar display 24 is narrow; its width is of between 10 and 20 mm. Like the monitor 22, the bar display 24 is substantially defined by a rectangle.

A transmit/receive probe 26 is connected to the housing through a plug type connection. Its structure is basically known, the reader is referred to the above mentioned German book for example. At its front end, it has a couplant 28. Here, the couplant 28 is implemented as a chamber filled with water and bounded by a thin plastic film, for example a latex film. The couplant 28 simultaneously is a preliminary distance. The couplant 28 permits to directly contact a workpiece 30 without inclusion of air bubbles and the like.

Here, the workpiece 30 is a portion of a sheet metal plate, the workpiece may also be two steel plates joined together by spot welding and so on. The workpiece 30 has an entrance surface 32, which is in contact with the couplant 28, and a backwall 34.

Eventually, the housing accommodates a transmitter 36 and a receiver 38. Both are connected to the probe 26. The transmitter periodically delivers transmit pulses that cause the probe 26 to deliver ultrasonic pulses. The individual ultrasonic pulses traverse the couplant 28. A fraction of each pulse is generally reflected at the entrance surface 32 and reaches as an entrance echo 40 the receiver in time before other signals. The receiver is connected to the monitor 22. The signal corresponding to the entrance echo 40 is visible on the monitor.

A fraction of each ultrasonic pulse generally penetrates the workpiece and is reflected at the backwall 34. It generally splits further and may return to the probe 26 through the entrance surface 32 after having been reflected once at the backwall; in parts however, it is also reflected at the entrance surface 32. The pulse is thereby typically reflected several times back and forth within the workpiece 30. This results in an echo sequence, namely an echo sequence of what are termed backwall echo signals with the first backwall echo 41, the second backwall echo 42, the third backwall echo 43 and so on 44, 45 being shown on the monitor.

Furthermore, a fraction of the ultrasonic pulse that has penetrated the workpiece is also reflected at flaws provided such flaws exist. An example of a flaw echo is shown at 50.

Monitor 22 displays what is termed an A-scan which in FIG. 4 is once more illustrated singly in a similar manner. The voltage U in Volts of the signals received is plotted down the side of the diagram on the y-axis whereas time T is plotted in seconds on the horizontal x-axis.

The bar display 24 displays information also shown in the A-scan of the monitor 22. Overall, three signal values are shown one above the other on the bar display 24. These signal values are displayed so as to be readily visible by an operator. The signal values are shown individually, the operator needs not gather at great expense the information from the A-scan as said information is directly shown in the form a bar. Accordingly, the bar display 24 serves to selectively show information contained in the A-scan. It shows a signal value 60 indicative of the quality of the entrance echo, a signal value 62 indicative of the quality of the backwall echo sequence and a signal value 64 indicative of the quality of the flaw echoes. The order of these three signal values is at the same time indicative of their hierarchy and priority respectively. In this context, the quality of the entrance echo is the most important information; the prerequisite of a good coupling is a sufficiently high entrance echo. The corresponding signal value of the entrance echo 60 is shown in yellow. The quality of coupling is sufficient when the entrance echo is above 100%. This means that in the A-scan the entrance echo runs beyond the upper edge of the monitor, as this is actually the case in the A-scan.

The signal value 62 for the quality of the backwall echo sequence is shown in green. It remains below 100% so that the yellow signal value of the entrance echo 60 will always remain visible. In the exemplary embodiment shown, the signal value 62 is approximately 86%. The height of the corresponding signal value is indicative of the quality of the backwall echo sequence. If the green bar reaches or exceeds an evaluation threshold to be prescribed by the adjuster, optimum coupling and quality of the backwall echo sequence has been achieved. The corresponding A-scan can be sent to the computer for evaluation.

Finally, a blue bar is shown, the corresponding signal value of the quality of the flaw echo 64 is relatively small; it remains below the other signal values 60, 62. In the illustration shown, the signal value 64 is approximately 14%.

It is thus possible to display three signal values 60, 62 and 64 one above the other on the same bar display 24. The voltage values for the signal values 60, 62 and 64 are obtained as follows:

A diaphragm 66 for the entrance echo 40 is provided for in the receiver 38. Said diaphragm 66 can be displaced as desired. It is adjusted by the operator in such a manner that the entrance echo falls into the diaphragm 66. The entrance echo obtained from every single ultrasonic pulse results in a voltage value in the receiver; if it falls within the range of the diaphragm 66, it is displayed on the bar display 24 as the signal value 60 of the entrance echo. Preferably, the bar display has, like the monitor 22, a scale in the direction of its y-axis, meaning of the voltage value. Thus, the electric voltage value of the entrance echo can be shown directly on the bar display 24 (provided it falls into the diaphragm 66).

For the backwall echoes 41, 42, . . . , 45 there is provided at least one diaphragm 68 with every single diaphragm 68 being preferably associated with a specific one of the backwall echoes. They register the voltage value of the maximum echo voltage. The signal value of the quality of the backwall echo sequence 62 is obtained from at least one voltage value, preferably from any mean taken from a plurality of voltage values or from the mathematical processing of a plurality of voltage values, and is displayed as described.

The same process is applied to the flaw echoes, these being associated with diaphragms 70 as well.

It is apparent from the above that the apparatus of the invention, and more specifically the method of inspecting workpieces carried out using the same, are suited for serial measurement. An example of serial measurement is the inspection of spot weld joints on bodyworks. The inspection apparatus is at first set at one workpiece or at a few workpieces prior to performing serial measurement.

The height of the various signal values 60, 62, 64 may be used to change settings of the inspection apparatus, more specifically to set the amplification of the receiver. If for example the signal value of the entrance echo 60 is less than 100%, it may be that the primary amplification is too low. Another reason may be bad coupling. If during initial setting of the inspection apparatus to to-be-tested serial workpieces one finds out that the signal value of the entrance echo 60 does not reach 100%, the primary amplification is too low and needs to be increased accordingly. An automatic amplification regulation may be provided to rectify the amplification.

An automatic amplification regulation may also be provided in order to influence, more specifically to increase, the amplification in such a manner that the signal value of the quality of the backwall echo sequence 62 is in a prescribed range of for example 80 plus or minus 15%. The amplification regulation takes into consideration that this value range is reached. The primary prerequisite is that the value of the entrance echo is in excess of 100%.

FIG. 2 shows another configuration of the apparatus. Now, the bar display 24 is no longer implemented as a separate part and is no longer disposed beside the monitor 22, although in closest proximity thereto; the bar display is now rather part of the surface of the monitor. Between the bar display 24 and the remainder of the monitor, a narrow space 72 in the form of a stripe extending from the top to the bottom has been left free in order to achieve a neat separation, said stripe may for example be a colour bar, an empty field or the like. In principle, the space 72 is not necessary, but it makes it easier for the operator to distinguish the fields into which the monitor 22 has been divided. Like the separate bar display 24, the integrated bar display of FIG. 2 is also disposed to the right side of the actual monitor.

FIG. 3 finally shows a bar display consisting of three rows of light-emitting diodes that are disposed side by side. Here, the various signal values 60, 62 and 64 are no longer displayed one above the other but rather side by side. Each row of light-emitting diodes has a different colour with row 74, which represents the signal value of the entrance echo 60 being for example yellow, the next row 75, which represents the signal value of the quality of the backwall echo sequence 62, red, and so on.

On the bar displays of the FIGS. 1 and 2, the signal values may be displayed side by side, partially superimposed or in another form.

Normalization of the backwall echo sequence will now be discussed herein after with reference to FIG. 5.

Normalization of the backwall echo sequence serves to qualitatively evaluate the intensity of the backwall echo amplitudes. A normalization level for the first backwall echo is prescribed, the corresponding value is Nn. The first backwall echo has an amplitude RWE(1) that is smaller than Nn. The difference Nn−RWE amplitude (1) is called the normalization difference Nd.

Backwall echo amplitudes that are the same or greater than 100% are summed up without normalization.

The parameter "normalization level Nn" is a variable and can be prescribed and varied as desired. This permits to influence the scaling of the arithmetic mean value that is displayed as the signal value 62 so that the latter can be allowed to be higher or lower. Normalization occurs using the following formulae:

$$Nd = Nn - RWEAmplitude\ (1) \tag{1}$$

$$NormAmp(i = 1) = \frac{100\% * RWEAmplitude\ (i = 1)}{Nn} \tag{2}$$

To normalize the amplitudes of the backwall echoes starting from the second backwall echo, the following "amplitude values An" are set up $$An(i>1)=RWEAmplitude(i>1)+Nd. \tag{3}$$

For An(3), the following applies for example $$An(3)=RWEAmplitude(4)+Nd$$

From the second backwall echo onward, the following normalization is carried out:

$$NormAmp\ (i = 1) = \frac{100\% * RWEAmplitude\ (i = 1)}{An\ (1 + i)} \tag{4}$$

The mean value of all the normalized backwall echoes, that is the signal value 62, is obtained using the following equation $$\overline{NormRWE} = \tag{5}$$

$$\frac{1}{n+m} * \left( \sum_{i=1}^{n} (RWEAmplitude \geq 100\%) + \sum_{i=1}^{m} NormAmp\ (i>1) \right)$$

To sum up it can be said that the invention has the following advantages: the inspection apparatus can be used wherever there is a need for a distinct echo sequence of the ultrasonic evaluation and/or measurements.

A coupling criterion for evaluating the coupling to the workpiece 30 is achieved, for example during inspection of spot weld joints. An additional indicator is obtained during digital wall thickness measurement. More specifically, it is important to know here whether the signal that is used for measuring contains a sufficient echo sequence at all.

Finally, by the step of normalizing echo sequences, an additional evaluation variable is achieved.

What is claimed is:

1. An ultrasonic inspection apparatus for non-destructive inspection of a work piece, the work piece having an entrance surface and a back wall, the ultrasonic inspection apparatus comprising:
   a transmit/receive probe, the transmit/receiver probe comprising a couplant for coupling to the entrance surface of the work piece, wherein the couplant allows for varying the angle under which the coupling to the entrance surface is performed in at least two solid angles,
   a transmitter connected to the transmit/receiver probe, the transmitter generating transmit pulses which it then delivers to the probe, wherein the transmit pulses, on the one side, are reflected at the entrance surface of the work piece back to the probe with an entrance echo pulse resulting there from and, on the other side, penetrate the work piece where they are reflected at least once at the back wall of the work piece with a back wall echo pulse resulting there from,
   a receiver connected to the probe, the receiver being suited for receiving the entrance echo pulse and the at least one back wall echo pulse and converting the received echo pulses to electric echo signals, and
   a bar display, the bar display being suited for showing at least one signal value in real time, with the signal value being derived from one of the following: the entrance echo, one back wall echo, a plurality of back wall echoes.

2. The ultrasonic inspection apparatus of claim 1, wherein the work piece under inspection further comprises flaws, the transmit pulses penetrating the work piece are also reflected at the flaws with flaw echoes resulting there from, and the bar display being suited for showing a signal value of a signal being derived from one of the following: the flaw echo of one selected flaw or the flaw echoes of a plurality of flaws.

3. The ultrasonic inspection apparatus of 1, with the bar display permitting to display in multiple colors, and at least two signal values, wherein the two signal values are displayed one above the other in different colors.

4. The ultrasonic inspection apparatus of claim 1, further comprising a monitor that is connected to the receiver for displaying the electric echo signals received from the receiver.

5. The ultrasonic inspection apparatus of claim 4, wherein the bar display is disposed proximate to the monitor.

6. The ultrasonic inspection apparatus of claim 4, wherein the monitor has a time axis and the bar display is disposed so as to extend transversely with respect to the time axis of the monitor.

7. The ultrasonic inspection apparatus of claim 4, wherein the monitor has a transverse dimension and the bar display has a length that equals the transverse dimension of the monitor.

8. The ultrasonic inspection apparatus of claim 4, wherein the monitor has a stripe-shaped area and the stripe-shaped area of the monitor is used as the bar display.

9. The ultrasonic inspection apparatus of claim 8, wherein the stripe-shaped area of the monitor is a border area of the monitor.

10. The ultrasonic inspection apparatus of claim 1, wherein the bar display is realized by a color LCD array.

11. The ultrasonic inspection apparatus of claim 1, wherein the work piece under inspection is composed of at least two sheet metal plates that are joined together by a spot weld joint, and the quality of the spot weld joint is to be determined.

12. A method for non-destructive inspection of a work piece, the work piece defining an entrance surface and a back wall, the method comprising the steps of:
   generating transmit pulses by means of a probe;
   delivering the transmit pulses to the entrance surface of the work piece, wherein the transmit pulses, on one side, are reflected at the entrance surface of the work piece back to the probe with an entrance echo pulse resulting there from and, on an opposite side, penetrate the work piece where they are reflected at least once at the back wall of the work piece with a back wall echo pulse resulting therefrom;
   receiving the entrance echo pulse and the at least one back wall echo pulse from a receiver and converting the received echo pulses to electric echo signals;
   displaying the electric echo signals received from the receiver on a monitor;
   showing at least one signal value in real time on a bar display, with the signal value being derived from one of (i) the entrance echo, (ii) one back wall echo, or (iii) a plurality of back wall echoes; and optimizing the coupling of the transmit pulses to the work piece by moving the probe in at least two solid angles and in absolute terms with respect to the work piece.

13. An ultrasonic inspection apparatus for non-destructive inspection of a work piece, the work piece having an entrance surface and a back wall, the ultrasonic inspection apparatus comprising:

a transmit/receive probe, the transmit/receiver probe comprising a couplant for coupling to the entrance surface of the work piece, wherein the couplant allows for varying the angle under which the coupling to the entrance surface is performed in at least two solid angles, a transmitter connected to the transmit/receiver probe, the transmitter generating transmit pulses which it then delivers to the probe, wherein the transmit pulses, on the one side, are reflected at the entrance surface of the work piece back to the probe with an entrance echo pulse resulting there from and, on the other side, penetrate the work piece where they are reflected at least once at the back wall of the work piece with a back wall echo pulse resulting there from, a receiver connected to the probe, the receiver being suited for receiving the entrance echo pulse and the at least one back wall echo pulse and converting the received echo pulses to electric echo signals, and a bar display, the bar display being suited for showing at least one signal value in real time, with the signal value being derived from the amplitude of one of the following: the entrance echo, one back wall echo, a plurality of back wall echoes.

\* \* \* \* \*